United States Patent [19]
Greene et al.

[11] Patent Number: 5,248,313
[45] Date of Patent: Sep. 28, 1993

[54] FIBULAR INTRAMEDULLARY ROD

[76] Inventors: Bruce L. Greene, 207 Lexington Ave.; Pastor Luciano, P.O. Box 2112, both of Passaic, N.J. 07055; Jurulu P. Rao, 100 Livingston Ave., Edison, N.J. 08820

[21] Appl. No.: 686,706

[22] Filed: Apr. 17, 1991

[51] Int. Cl.⁵ .................................... A61F 5/00
[52] U.S. Cl. .................................. 606/62; 606/60; 606/64
[58] Field of Search ............ 606/53, 60, 62, 63, 606/64, 67, 86, 95, 96, 98

[56] References Cited

U.S. PATENT DOCUMENTS

| | | | |
|---|---|---|---|
| 4,475,545 | 10/1984 | Ender | 606/604 |
| 4,550,449 | 11/1985 | Tunc | 606/60 X |
| 4,622,959 | 11/1986 | Marcus | 606/98 X |
| 4,805,607 | 2/1989 | Engelhardt et al. | 606/67 |
| 4,895,572 | 1/1990 | Chernoff | 606/64 X |
| 4,913,137 | 4/1990 | Azer et al. | 606/96 X |
| 5,034,013 | 7/1991 | Kyle et al. | 606/63 X |
| 5,041,115 | 8/1991 | Frigg et al. | 606/62 |

FOREIGN PATENT DOCUMENTS 1031128 3/1953 France ...................... 606/62

*Primary Examiner*—Danton D. DeMille
*Assistant Examiner*—Sam Rimell
*Attorney, Agent, or Firm*—John G. Gilfillan, III

[57] ABSTRACT

A novel fibular intramedullary rod obviates the need to use bone plates to treat fibular fractures. The rod comprises a solid or cannulated elongated member which is insertable upwardly into the fibular medullary canal. The proximal portion of the rod is smaller in diameter than the tapered distal portion which may be obliquely truncated. The rod is slightly curved or bowed and provided with screw receiving transverse holes.

23 Claims, 3 Drawing Sheets

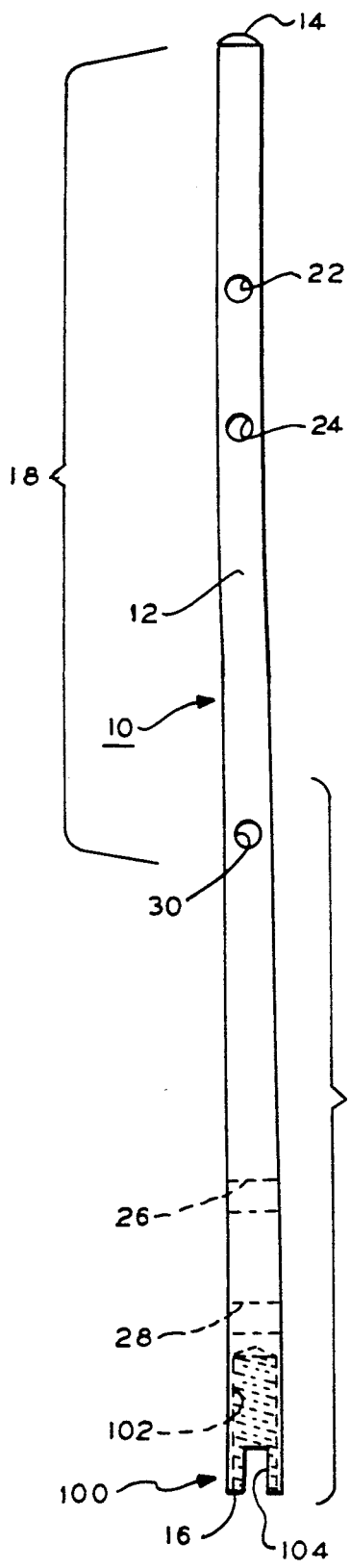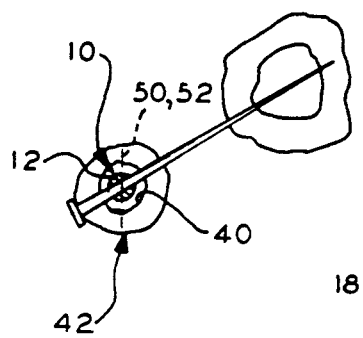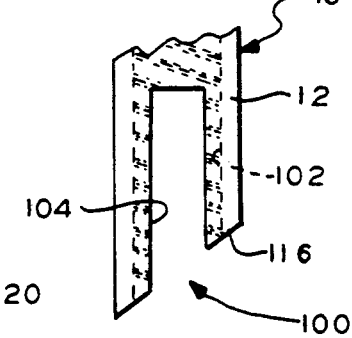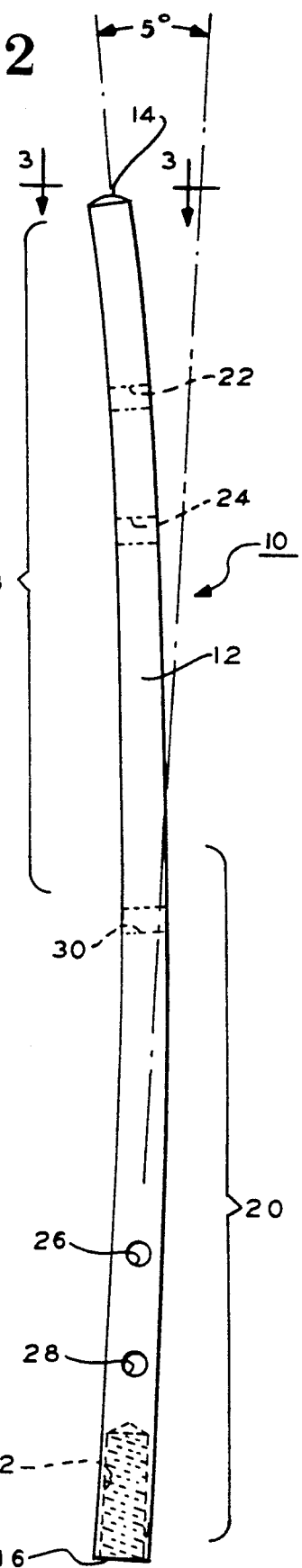

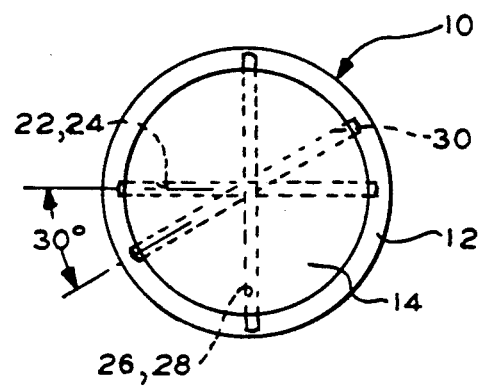
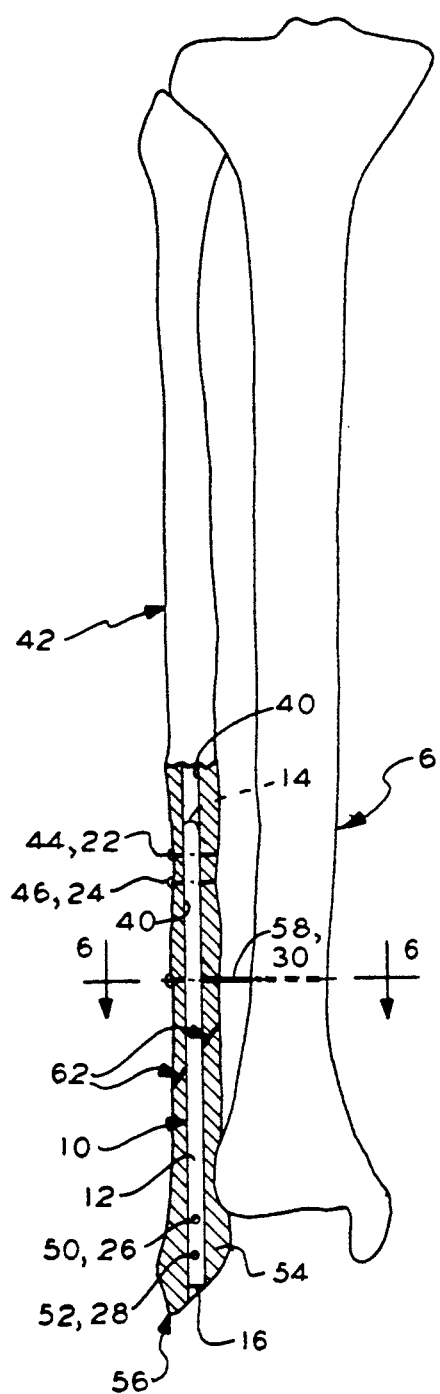
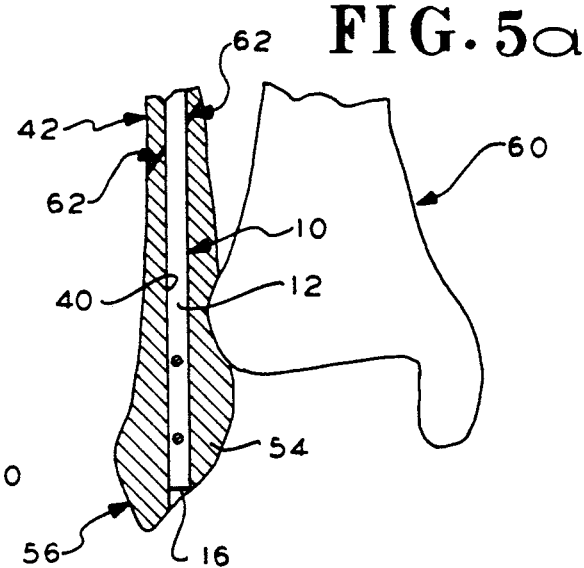
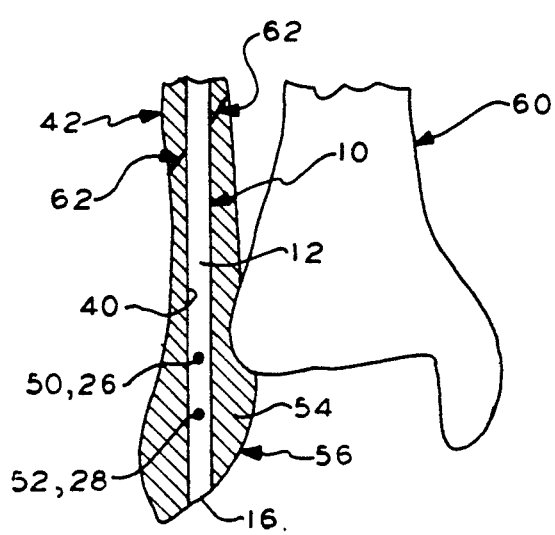

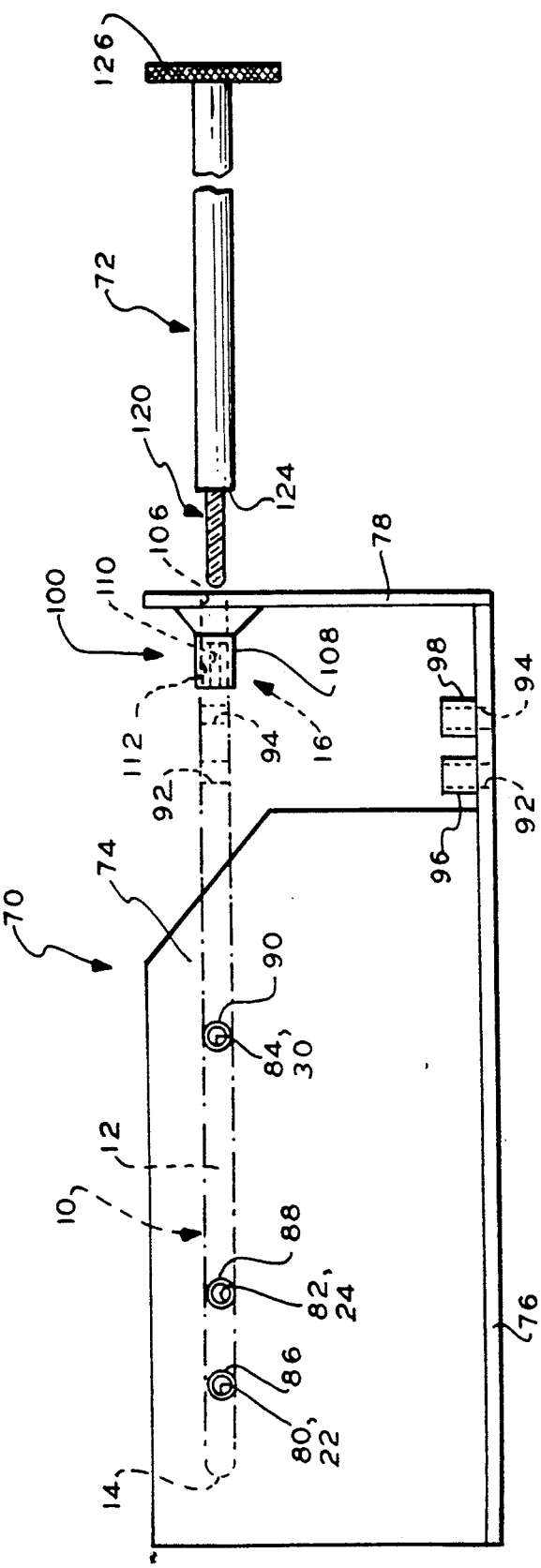
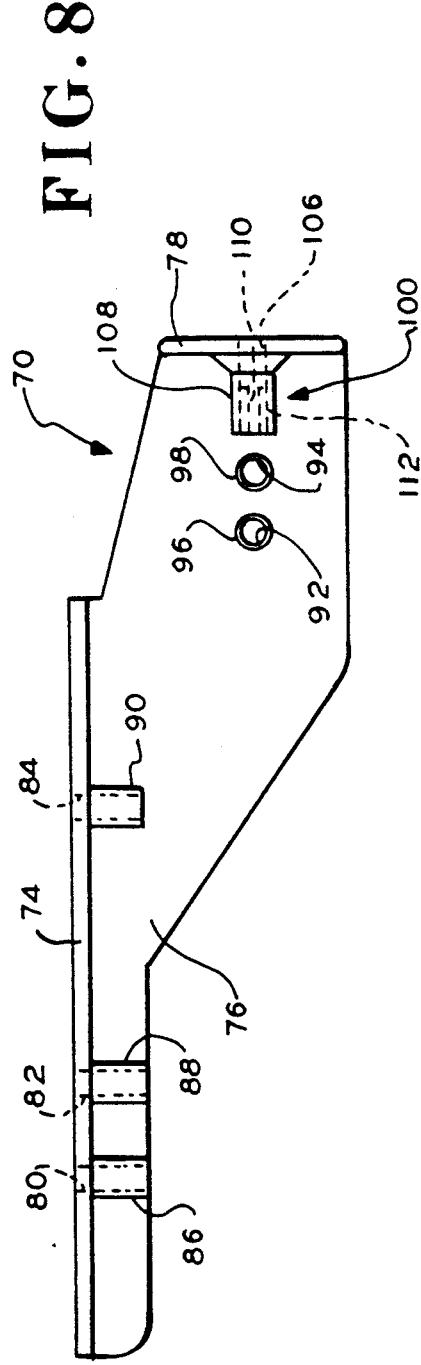

FIBULAR INTRAMEDULLARY ROD

BACKGORUND OF THE INVENTION

The present invention relates to an intramedullary rod or nail for use in a fractured fibula.

The use of intramedullary rods or nails in treating fractures of the femur, tibia and other "long" bones is well known, see U.S. Pat. No. 4,875,474. Such a rod or nail is inserted into the medullary canal or marrow space of a fractured bone so as to bridge the fracture and then, after the fracture is reduced (the opposed cortices are aligned, mated and compressed), bone screws or other fasteners are driven into the bone's lateral cortex and through corresponding holes or openings in the rod. The rod or nail fixates or immobilizes the fracture and maintains reduction (compression) thereof. See U.S. Pat. No. 4,881,535. When bone screws are used at or near both opposed ends of the rod, relative rotation of the bone on either side of the fracture is prevented, as are shortening or lengthening of the bone and the fracture. See U.S. Pat. No. 4,475,545.

Intramedullary rods are typically inserted into the fractured bone via a small incision through overlying tissue. After insertion, the rod, which is not directly observable, may be oriented and the holes therein may be located by means of a jig which is attachable to an end of the rod at the incision and resides outside of the body. Rod-jig attachment is typically achieved by facilities which maintain a known, predefined positional relationship between the rod and the jig. In this fashion a predetermined location on the jig, such as that holding a drill guide, bears a known relationship to a site on the rod, such as a screw hole, or an area of the bone, such as a drilling site. See U.S. Pat. Nos. 4,913,137; 4,622,959; 4,911,153; 4,827,917.

Prior to the use of intramedullary rods and screws, fractured "long" bones were fixated with bone plates. Such plates typically covered a selected amount (often about 120°) of the external lateral cortex of the fractured bones and all the fragments thereof in the vicinity of the fractures. The plates were attached to the bone fragments by bone screws passing through screw holes in the plate and into the bone cortex. See U.S. Pat. No. 4,913,137.

The use of bone plates requires large operative openings, which involves an attendant increased risk of infection. Also, bone plates must often be removed after several years due to ultimate bone weakening caused by the screws therein. Removal, of course, requires a second operative opening. These shortcomings led to the development of the above-described intramedullary rods or nails.

Fractures of bones which are not "long" bones have continued to be treated with bone plates. The present preferred method of reducing an acute (unstable and/or displaced) fibular or ankle fracture, including a fracture in or near the lateral mulleolus of the fibula, is the use of such a bone plate. The use of bone plates to reduce fractured fibulas suffers from the above-noted problems. Additionally, because there is little skin and soft tissue covering a fibular bone plate, the wound resulting from closure of the operative placement opening frequently dehisces, especially if the patient has a history of diabetes or vascular insufficiency. Moreover, the screw head, if elevated above the plate, and the plate itself can wear through the overlying soft tissue and skin to create a new wound. Dehiscence of the old wound or opening of a new wound raise the possibility of infection. Additionally, the bones of some patients, particularly elderly patients suffering from osteoporosis and other patients whose bones have experienced demineralization, do not hold bone screws either well or for long periods due to the lack of sufficient screw-holding cortical mass. This may lead to the screws loosening or pulling out and resultant destabilization of the fracture.

SUMMARY OF THE INVENTION

The present invention has as a major objective the provision of a fibular intramedullary rod which obviates the need to use bone plates to treat fibular fractures, especially acute ankle fractures in the vicinity of the distal malleolus.

With this objective in mind, the rod of the present invention comprises a solid or cannulated elongated member which is insertable upwardly into the fibular medullary canal through a small incision at the top of the foot and the distal malleolus. The tubular member may be made in whole or in part of stainless steel, titanium, rigid plastics or polymers and biodegradeable materials.

The rod has an upper proximal portion and lower distal portion. The proximal portion has a smaller width or diameter than the distal portion, and the distal portion is preferably tapered. The rod is slightly curved or bowed medially-to-laterally, preferably by about 5°. The distal end of the rod may be obliquely truncated to conform to the contour of the distal fibular malleolus and to not protrude into and deleteriously affect the malleolus-talus interfacial area of the ankle joint.

The rod includes proximal and distal, transverse holes therethrough. The proximal extend in a lateral-to-medial direction; the distal holes extend in an anterior to posterior direction. A third hole is formed through the rod with its axis angularly displaced anteriorly-to-posteriorly from the proximal holes by an acute angle, preferably about 30°.

After insertion of the rod into the fibular medullary canal and temporary reduction of the fracture has been achieved, bone screws are driven laterally-to-medially into the fibular cortex above the fracture and through the proximal holes. Bone screws are also driven in an anterior-posterior direction through the distal holes and the portion of the fibula below the fracture, i.e., in or near the distal fibular malleolus. Since the distal screws are oriented in a anterior-to-posterior direction, entry thereof into the ankle joint is minimized if not obviated. Moreover, the 90° angle between the proximal holes and the distal holes maximizes purchase of the bone screws because of the relative mass and density of the distal fibular malleolus.

The slight curvature or bowing of the rod causes three-point contact between the rod and the walls of the fibular medullar canal. This three-point contact tends to longitudinally and rotationally stabilize the rod even before the screws are driven and acts in aid of the screws to fixate and reduce the fracture after the screws are driven.

A syndesmotic screw is driven through the third hole and the surrounding lateral fibular cortex and then into and through the lateral cortex of the tibia. The syndesmotic screw stabilizes the fracture and the tibular fragments on either side thereof. The angular displacement of the third hole from the axes of the other holes is such as to facilitate this interconnection of the fibula and tibia.

Once the rod has been inserted into the fibula, proper longitudinal and angular positioning of the rod and its holes may be achieved by a jig or fixture which has a defined known spatial relationship to the rod when the two are attached in a predetermined manner. The jig may also be used to located the holes in the rod and to locate and drill holes in the bones prior to driving bone screws thereinto.

BRIEF DESCRIPTION OF THE DRAWING

FIG. 1 is a side elevation of an intramedullary pin for use in a fractured right fibula according to the present invention as viewed from the patient's right side;

FIG. 2 is a front elevation of the intramedullary pin of FIG. 1 as viewed from the patient's front;

FIG. 3 is a magnified top view of the intramedullary pin shown in FIGS. 1 and 2 taken from the proximal or upper end thereof along line 3—3 in FIG. 2;

FIG. 4 depicts an alternative distal end for the pin as it is shown in FIGS. 1-3;

FIG. 5 is a posterior-to-anterior depiction of a fractured right fibula and an adjacent right tibia illustrating the use of the pin of the present invention in FIGS. 1-3 as shown from the front of the patient;

FIGS. 5a and 5b are enlarged views of the distal malleolus of the right fibula shown in FIG. 5 and showing, respectively, the distal end of the pin hereof according to FIGS. 1-3 and FIG. 4;

FIG. 6 is a top view taken along line 6—6 in FIG. 5 showing the proximal end of the pin of FIGS. 1-3 following insertion of the pin into a fractured fibula;

FIG. 7 is a front elevation of a jig which is usable with the pin of the present invention to insert the pin into a fractured fibula, to orient the pin and to drill necessary holes in to the fibular and tibial cortices for screws which anchor the pin; and FIG. 8 is a plan view of the jig of FIG. 7.

DETAILED DESCRIPTION

A preferred embodiment of a pin 10 according to the present invention is shown in FIGS. 1-3. The pin 10 finds particular use in fixating fractured fibulas, particularly in elderly patients suffering from osteoporosis or in other patients whose bones have experienced demineralization. The cortices of the bones of such patients typically have insufficient mass and volume to permit fractures to be satisfactorily fixated using standard techniques, such as bone plates. Moreover, techniques utilized with so-called "long" bones, such as the femur and tibia, have, until now not been usable or adaptable for use with smaller bones, such as the fibula.

The pin 10 comprises as elongated member 12 made of a material which is benign to the human body and possesses sufficient tensile and compressive strength to satisfactorily fixate a fibular fracture. The pin may be fabricated from materials such as stainless steel, titanium, polymers, or biodegradable materials which, after a period of time in the human body break down or dissolve. Those skilled in the art will appreciate that the material chosen will be one having the requisite strength for fracture fixation in the manner hereinafter described. The material chosen will also not cause adverse reactions in human bodies once emplaced therein and will also be more or less immune to attack by body fluids and tissues, except to the extent that such is intentionally desired, as will be the case with biodegradeable materials.

In order not to have to stock pins 10 of numerous lengths, a typical length for the pin 10 is about 5.25 inches. This length has been found to permit fibular fracture fixation in a wide variety of patients. Other lengths may, of course, be selected depending on known criteria.

The member 12 comprises a proximal end 14 and a distal end 16. With reference to an erect, standing patient, "proximal" means upper and "distal" means lower. The member also includes a proximal section 18 extending from the proximal end 14 toward the distal end 16 and a distal section 20 extending from the distal end 16 toward the proximal end 14. In a preferred embodiment, the proximal section 18 is about 2.75 inches long and the distal section 20 is about 2.50 inches long.

Although the member 12 may have a variety of cross-sections, for ease of manufacture and insertion it is preferred that it have a substantially round cross-section. Preferably, the width or diameter of the proximal section 18 is approximately 4.7 mm (0.185 inch); the width or diameter of the distal section 20 smoothly tapers from the width or diameter of the proximal section 18 to a width or diameter of about 5.1 mm (0.20 inch) at the distal end 16.

The foregoing dimensions and the amount of taper have been found to permit convenient insertion of the pin 10 through the distal fibular malleolus and into the fibular medullas of a broad spectrum of patients, while resulting in the pin 10 being easily stabilized following insertion. Specifically, the smaller width or diameter of the proximal end and section 14 and 18 permits insertion of the pin 10 into the fibular medullar canal through the distal malleolus and thereafter upwardly to a position above the fracture. The larger, tapered distal section 20 may be fixedly located within the medullar canal below the fracture.

Again, as with the length of the pin 10, it is obvious that the foregoing dimensions and the amount and degree of the taper may be adjusted as necessary or desirable in particular or general situations which differ from the norm. The tapered-nontapered or two-stage design has been observed to permit good purchase of the canal walls by the pin 10 and a better fit in the canal. This is because the taper mirrors a general distal-to-proximal narrowing of the fibular medullary canal which has been observed in many patients particularly the elderly whose bones have experienced osteoporosis. Further, unlike the "long" bones, the fibula is ordinarily too small to permit reaming of the medullary canal prior to emplacement of the pin 10. The taper of the member 12 permits the pin 10 to be driven into the unreamed canal.

As best shown in FIG. 2, the member 12 is preferably slightly bowed of curved. This slight bowing or curvature is medial-to-lateral, when viewed from the front of the pin 10, that is, in an anterior-to-posterior direction relative to a patient. Since the pin 10 in FIG. 2 is intended for use in a right fibula, a similar pin 10 for use in a left fibula would be oppositely bowed. Although the bowing may be isolated to specific segments of the member 12, it has been found preferably to have the bowing smoothly extend along the entire length of the member 12. In a specific embodiment, the bowing is about 5°. Since the medullary canal of a bone is a generally tubular passageway, the bowing permits the pin 10 to be frictionally engaged or fixated within the canal at three points, namely, where the ends 14 and 16 of the member 12 abut the canal and where the intermediate mid-point of the bowed member 12 abuts the canal.

The member 12 may be solid or cannulated. Where it is cannulated it may, as is well known be emplaced with the aid of a guide wire or the like. A preferred guide wire has a diameter of 1.35 mm (0.053 inch), and the passageway through the member would be sized accordingly. Although the drawing depicts only a solid member 12, it is understood that a cannulated member 12 is within the skill of the art.

Still referring to FIGS. 1–3, the member 12 includes holes 22, 24 and 26, 28 therethrough in its proximal and distal sections 18 and 20, respectively. The diameters of the holes 22, 24 in the proximal section 18 are about 2.0 mm, and the diameters of the holes through the distal section 20 are about 2.7 mm in diameter. These diameters are adjustable to accommodate screws of varying diameters, it being preferred that the screws pass through the holes without threadingly or significantly frictionally engaging the walls of the holes 22, 24, 26, 28. Preferably, the screws pass through the holes 22, 24, 26, 28 freely but without significant clearance.

As shown in FIGS. 1–3, the proximal holes 22, 24 are oriented in a lateral-to-medial direction. This permits passage of bone screws through the diametrically opposed cortex walls and the holes 22, 24 in a lateral-to-medial direction. The distal holes 26, 28 are oriented in an anterior-to-posterior direction, that is, perpendicular to the direction of the holes 22, 24. This permits bone screws to be driven in an anterior-to-posterior direction through the diametrically opposed cortex walls of the fibula in the vicinity of the distal malleolus. It has been observed that the fibula in this area has substantially better bone density and quality in the anterior-to-posterior direction than it does in the lateral-to-medial direction. Moreover, the possibility is quite low, if not non-existent, that screws passing through the fibular cortex and the holes 26, 28 in the anterior-to-posterior direction will enter the ankle joint.

Formed through the member 12 generally intermediate the ends 14 and 16 is a hole 30 for a syndesmotic screw. The hole 30 is intended to permit a syndesmotic screw to be driven therethrough and through the diametrically opposed cortical areas of a fibula and into the cortex of an adjacent tibia to stabilize the fracture. The direction of the hole 30 may be any that permits the syndesmotic screw to stabilize the fracture. It has been found that a preferred direction is one that angularly located relative to the holes 22, 24 by 30° in the anterior-to-posterior direction. It is also preferred that the hole 30 be located along the length of the member 12 so as to be above the fracture of the fibula when the pin 10 is emplaced (see FIG. 5).

Fewer or more holes 22, 24, 26, 28, 30 may be used as dictated by the circumstances. Those skilled in the art will appreciate the factors determining both the number and placement of such holes 22–30. In a preferred embodiment of the pin 10, wherein an attempt has been made to accommodate a variety of patients, the most proximal hole 22 is about 1 inch from the proximal end 14 and the adjacent hole 24 is about 0.5 inch away therefrom. The most distal hole 28 is about 0.6 inch from the distal end 16 and the adjacent hole 26 is about 0.45 inch away therefrom. The syndesmotic screw hole 30 is about 2.3 inch from the distal end 16. The foregoing dimensions may be varied to meet varying conditions, as is obvious.

FIGS. 5 and 6 show, somewhat schematically, the pin 10 following its emplacement in the medullary canal 40 of a right fibula 42, as seen from the front of a patient or anteriorly-to-posteriorly. Screws 44, 46 have been driven through both diametrically opposed walls of the fibular cortex 48 and through the proximal holes 22, 24 in a lateral-to-medial direction. Screws 50, 52 have been driven through both diametrically opposed walls of the cortex 54 of the distal fibular malleolus 56 and through the distal holes 26, 28 in a anterior-to-posterior direction. A syndesmotic screw 58 has been driven through the opposed walls of the fibular cortex 48 and through the hole 30 into the cortex of the adjacent tibia 60 in a general anterior-to-anterior direction making an angle of about 30° with the screws 22, 24 (see FIG. 6). The pin 10 and the screws 22–30 stabilize and fixate a fracture 62 in the fibula 42 to permit healing thereof.

As seen in FIGS. 5 and 5a, the distal end 16 of the member 12 is positioned far enough into the canal 40 so as not to protrude into the area of the ankle joint below the malleolus 56. In an alternative embodiment shown in FIGS. 4 and 5b, the distal end 16 of the member 12 is obliquely truncated so that it matches the contour of the distal malleolus 56 and may be positioned within the end so as to be flush therewith.

FIGS. 7 and 8 illustrate a jig 70 and a locking pin 72 for use with the rod 10. The jig 70 is for use with the pin 10 to be inserted into a right fibula 42. A jig for inserting the pin 10 into a left fibula 42 will, as is apparent, be a mirror image of the jig 70.

The jig 70 includes a first plate 74 integrally formed with a second plate 76 perpendicular thereto. Integral with the second plate 76 is a third plate 78 which is perpendicular to both plates 74 and 76. The first plate 74 contains holes 80, 82 and 84 surrounded by raised tibular bushings or drill guides 86, 88 and 90. The holes 80–84 and the guides 86–90 are so dimensioned that a bone drill located therein is accurately located for precise drilling in a direction determined by the direction of the axes thereof. Screw holes through the fibular cortex for the proximal screws 44, 46 are drilled with the hole-guide pairs 80–86 and 82–88. The screw holes through the fibular and tibial cortices for the syndesmotic screw 58 are drilled using the hole-guide pair 84–90.

The second plate 76 contains holes 92 and 94 surrounded by raised drill guides 96 and 98. The hole guide pairs 92–96 and 94–98 are dimensioned to facilitate drilling of the cortical screw holes through the malleolus 56 for the distal screws 50 and 52.

As is well known, the pin 10 and the jig 70 are physically related or locked together in a selected fashion before the pin 10 is driven into the fibular medullary canal 40. This relationship is such that the hole-guide pairs 80–86, 82–88, 84–90, 92–96 and 94–98 are respectively precisely aligned with the holes 22, 24, 30, 26 and 28 in the member 12. After the pin 10 is driven into the canal 40, the jig 70 overlies the patient's leg and is first used to position the pin 10 within the canal 40 and to thereafter drill the cortical screw holes.

Although any known technique for locking the pin 10 and the jig 70 together may be used, it is preferred that the relevant facilities do not require that the distal end 16 of the member 12 or the adjacent regions of the distal section 20 are enlarged. Any enlargement at or near the distal end 16 may increase the difficulty of fully driving the pin 10 into the canal 40, thus increasing the possibility that the pin 10 may protrude into the ankle joint below the malleolus 56.

The preferred facilities 100 for locking together the pin 10 and the jig 70 are shown in FIGS. 1, 2, 4, 7 and 8. These facilities 100 may include: (a) axial and hreaded bore 102 formed through the distal end 16 of the pin 10, (b) notches or key ways 104 normal to and intersecting the bore 102, 9c) a hole 106 through the third plate 78 of the jig 70, (d) a raised tubular bushing 108 surrounding the hole 106 and (e) protruding keys or projections 110 on the wall of a passageway 112 through the bushing 108 and continuous with the hole 106. The passageway 112 permits the distal end 16 of the pin 10 to be snugly held therein and to be rotated until the keys 110 fit into the notches 104 and rotationally hold the pin 110. The keys 110, notches 104 and holes 22–30 are located so that this results in the holes 22–30 and the hole-guide pairs 80–86, etc. being respectively precisely aligned. Thereafter, a threaded end 120 of the locking pin 72 is run through the hole 106 and the passageway 112; the locking pin 72 is rotated and the end 120 is threaded into the threaded bore 102 until a shoulder 124 on the locking pin 122 abuts the third plate 78 to longitudinally hold the pin 10. The locking pin 72 may have an enlarged end 126 to which appropriate force may be applied for driving the pin 10 into the canal 40. The end 126 may be knurled to facilitate its rotation for locking and unlocking the pin 10 and the jig 70.

What is claimed is:

1. An intramedullary rod for use in fixating a fibular fracture located in the vicinity of the lateral malleolus, which comprises:

an elongated member having between its distal and proximal ends a distal section and an integral proximal section, the proximal section and end being insertable and movable through the distal fibular malleolus into the fibular medullary canal to occupy a position above the fracture, the distal section and end being insertable into the fibular medullary canal through the fibular malleolus to occupy a position below the fracture;

wherein, (i) the proximal section includes a lateral-to-medial first hole formed through the member with its axis generally perpendicular the axis of the member, (ii) the distal section includes an anterior-to-posterior second hole formed through the member with its axis generally perpendicular to the axes of the member and the first hole, the first and second holes being capable of respectively accepting lateral-to-medial and anterior-to-posterior bone screws driven into diametrically opposed areas of the fibular cortex, and (iii) the member includes, generally longitudinally centrally disposed between the first and second holes, a third hole formed therethrough and having an anterior-to-posterior axis which is perpendicular to the axis of the member and which makes an acute anterior-to-posterior angle with the axis of the first hole, the third hole being capable of accepting a syndesmotic screw driven through the fibular cortex and into the cortex of an adjacent tibia.

2. An intramedullary rod as in claim 1, wherein there are at least two spaced first holes and two spaced second holes, the axes of the first holes being mutually parallel, the axes of the second holes being mutually parallel.

3. An intramedullary rod as in claim 1, wherein the member is made of a material selected from the group consisting of stainless steel, titanium, polymers and biodegradeable materials.

4. An intramedullary rod as in claim 1, wherein at least a portion of the member is slightly bowed medially-to-laterally.

5. An intramedullary rod as in claim 4, wherein the slight bowing of the member occurs over the length thereof.

6. An intramedullary rod as in claim 5, wherein the slight bowing of the member is approximately 5°.

7. An intramedullary rod as in claim 1, wherein the member is tapered and the width of the proximal end is smaller than the width of the distal end.

8. An intramedullary rod as in claim 7, wherein the member has a generally circular cross-section and the widths are diameters.

9. An intramedullary rod as in claim 6, wherein:
    the diameter of the proximal section is equal to the diameter of the proximal end and is substantially constant along the length thereof, and
    the diameter of the distal section gradually increases from the diameter of the proximal section to the diameter of the distal end.

10. An intramedullary rod as in claim 9, wherein:
    the diameters are selected so as to permit insertion of the member into the fibular intramedullary canal.

11. An intramedullary rod as in claim 10, wherein:
    the proximal section is approximately 2.75 inches long and has a diameter of approximately 4.7 mm, and
    the distal section is approximately 2.50 inches long, is generally, smoothly tapered, and varies in diameter from 4.7 mm to 5.1 mm at the distal end.

12. An intramedullary rod as in claim 1, wherein the member is solid.

13. An intramedullary rod as in claim 1, wherein the member is cannulated to accept and be used with a guide wire during insertion into the fibular medullary canal.

14. An intramedullary rod as in claim 1, wherein:
    the member is slightly bowed medially-to-laterally sufficient amount to achieve three-point fixation of the member within the fibular medullary canal, such fixation being due to engagement between the fibular canal walls, on the one hand, and the ends of the member and a portion of the member between the ends, on the other hand.

15. An intramedullary rod as in claim 1, wherein the angle between the axes of the first and third holes is approximately 30°.

16. An intramedullary rod as in claim 1 for use with a jig by which the holes are locatable and via which drilling through the fibular and tibial cortices is guided in alignment with such holes, which further comprises:
    means on the distal end of the member and selectively engageable with the jig for relatively orienting the member and the jig in a predetermined manner so that locating the holes in the member has been inserted into the fibular medullary canal.

17. An intramedullary rod as in claim 1, wherein:
    the distal end of the member is obliquely truncated so as to be generally complementary in contour to the contour of the fibular malleolus at the point of insertion of the member into the fibular medullary canal.

18. An intramedullary rod for use in fixating a fibular fracture located in the vicinity of the lateral malleolus, which comprises:

an elongated member having between its distal and proximal ends a distal section and an integral proximal section, at least a portion of the tube being slightly curved or bowed medially-to-laterally, the proximal section having a smaller lateral dimension than the distal section, the proximal section and end being insertable into and movable through the distal fibular malleolus into the fibular medullary canal to occupy a position above the fracture, the distal segment and end being insertable into the fibular medullary canal through the fibular malleolus to occupy a position below the fracture;

wherein (i) the proximal segment includes a plurality of parallel, lateral-to-medial first set of holes formed through the member and spaced apart along the member with their axes generally perpendicular the axis of the member, (ii) the distal segment includes a plurality of parallel, anterior-to-posterior second set of holes formed through the member and spaced apart along the member with their axes generally perpendicular to the axes of the member and the first set of holes, the first and second hole sets being capable of respectively accepting lateral-to-medial and anterior-to-posterior bone screws driven into diametrically opposed areas of the fibular cortex, and (iii) he member includes generally longitudinally centrally disposed between the first and second hole sets, a third hole formed therethrough and having an anterior-to-posterior axis which makes an acute anterior-to-posterior angle with the axes of the first hole set, the third hole being capable of accepting a syndesmotic screw driven through the fibular cortex and into the cortex of an adjacent tibia.

19. An intramedullary rod for use in infixating a fibular fracture located in the vicinity of the lateral malleolus which comprises:

an elongated member made of stainless steel, titanium, a polymer or a biodegradeable material, the member having between its distal and proximal ends a distal section and an integral proximal section; at least a portion of the member being slightly bowed medially-to-laterally by an angle of about 5° to achieve three-point fixation of the member within the fibular medullary canal, such fixation being due to engagement between the fibular canal walls, on the one hand, and the ends of the member and a portion of the member between the ends, on the other hand; the member being tapered with the width of the proximal end being smaller than the width of the distal end; the proximal section and end being insertable and movable through the distal fibular malleolus into the fibular medullary canal to occupy a position above the fracture; the distal section and end being insertable into the fibular medullary canal through the distal fibular malleolus to occupy a position below the fracture;

wherein (i) the proximal section includes a plurality of parallel, lateral-to-medial first set of holes formed through the member and spaced a part along the member with their axes generally perpendicular to the axis of the member, (ii) the distal section includes a plurality of parallel, anterior-to-posterior second set of holes formed through the member and spaced apart along the member with their axes generally perpendicular to the axes of the member and the first hole set, the first and second hole sets being capable of respectively accepting lateral-to-medial and anterior-to-posterior bone screws driven into diametrically opposed areas of the fibular cortex, and (iii) the member includes, generally longitudinally centrally disposed between the first and second hole set, a third hole formed therethrough and having an anterior-to-posterior axis which makes an anterior-to-posterior angle of about 30° with the axes of the first holes the third hole being capable of accepting a syndesmotic screw driven through the fibular cortex and into the cortex of the adjacent tibia; and means associated with the distal end of the member for orienting the inserted member within the fibular medullary canal, for determining the location of the holes, and for guiding drilling through the cortices in alignment with the holes.

20. An intramedullary rod as in claim 19, wherein:

the member has a generally circular cross-section and the widths are diameters, the diameter of the proximal section being equal to the diameter of the proximal end and being substantially constant along the length of the first section, the diameter of the distal section gradually increasing from the diameter of the proximal section to the diameter of the distal end.

21. An intramedullary rod as in claim 20, wherein the diameter of the first end is about 4.7 mm, the diameter of the second end is about 5.1 mm, the length of the first section is about 2.75 inches and the length of the second section is about 2.50 inches.

22. An intramedullary rod as in claim 21, wherein the member is solid.

23. An intramedullary rod as in claim 22, wherein the member is cannulated to accept and be used with a guide wire during insertion into the fibular medullary canal.

* * * * *

UNITED STATES PATENT AND TRADEMARK OFFICE
CERTIFICATE OF CORRECTION

PATENT NO. : 5,248,313

DATED : September 28, 1993

INVENTOR(S) : Bruce L. Greene, Pastor Luciano and Jurulu P. Rao

It is certified that error appears in the above-indentified patent and that said Letters Patent is hereby corrected as shown below:

Col. 7, line 5, change "hreaded" to
--threaded--.

Col. 9, line 26, change "he" to --the--.

line 30, after "which" insert:
--is perpendicular to the axis of the
member and which--.

line 35, change "infixating" to --fixating--.

Col. 10, line 7, change "a part" to --apart--.

line 22, after "which" insert:
--is perpendicular to the axis of the
member which--.

Signed and Sealed this

Ninth Day of August, 1994

Attest:

BRUCE LEHMAN

Attesting Officer

*Commissioner of Patents and Trademarks*